United States Patent [19]

Burkhardt et al.

[11] 4,059,559

[45] Nov. 22, 1977

[54] PROCESS FOR PREPARING N-TRIORGANOSILYLCARBAMIDE ACID ESTERS

[75] Inventors: Jürgen Burkhardt; Paul Hittmair; Karl-Heinrich Wegehaupt, all of Burghausen, Germany

[73] Assignee: Wacker-Chemie GmbH, Munich, Germany

[21] Appl. No.: 603,413

[22] Filed: Aug. 11, 1975

[30] Foreign Application Priority Data

Oct. 7, 1974    Germany ............................ 2447707

[51] Int. Cl.$^2$ .............................................. C07F 7/10
[52] U.S. Cl. .............................................. 260/448.2 E
[58] Field of Search ................................... 260/448.2 E

[56] References Cited

U.S. PATENT DOCUMENTS 2,876,209    3/1959    de Benneville et al. ... 260/448.2 E X Primary Examiner—Paul F. Shaver

[57] ABSTRACT

An improved process for preparing N-triorganosilylcarbamide acid esters by reacting in the substantial absence of a solvent a carbamide acid ester having two hydrogen atoms linked to the nitrogen atom with a hexaorganodisilazane and a triorganohalosilane and thereafter separating the resultant N-triorganosilylcarbamide acid ester from ammonium halide.

12 Claims, No Drawings

PROCESS FOR PREPARING N-TRIORGANOSILYLCARBAMIDE ACID ESTERS

The present invention relates to N-triorganosilylcarbamide acid esters and more particularly to an improved process for preparing N-triorganosilylcarbamide acid esters in the substantial absence of a solvent.

Heretofore, it has been known that N-triorganosilylcarbamide acid esters, i.e., esters which can, for example, also be referred to as N-triorganosilylcarbaminic acid esters or as N-triorganosilylcarbamates, can be prepared by reacting a carbamide acid ester with a triorganohalosilane in the presence of a trialkylamine (see G. Greber et al "Eine neue Isocyanate und Isothiocyanate Synthese" in "Angewandte Chemie", Volume 80, 1968, pp 1028/1029).

However, this process has certain disadvantages. For example, it can be carried out only in the presence of large amounts of solvent since large amounts of trialkylaminohydrohalide are produced. It is therefore essential that the N-triorganosilylcarbamide acid esters be purified by distillation.

Also, it is known that N-triorganosilylcarbamide acid esters can be prepared by reacting a carbamide acid ester with a triorganosilylorganoamine (see U.S. Pat. No. 2,876,209 to de Benneville et al, issued Mar. 3, 1959). This process, which has been referred to as "reaminization" can be performed without a solvent, however, it has the disadvantage that it requires relatively high temperatures which in turn produces a large amount of by-products in addition to the amine. Also, it is essential that the products from this process be distilled in order to obtain pure N-triorganosilylcarbamide acid esters.

Applicants have attempted to produce N-triorganosilylcarbamide acid esters by reacting a carbamide acid ester such as one corresponding to the formula $H_2NCOOR'$, where $R'$ represents a methyl, ethyl, propyl or n-butyl radical, with a hexaorganodisilazane at a temperature of from 100° to 130° C. The resultant N-triorganosilylcarbamide acid esters were contaminated with a considerable amount of by-products such as triorganoalkoxysilane, cyanuric acid and urea. In the purification of the resultant product by distillation, a portion of the desired ester decomposed.

Furthermore, it is known that an N-triorganosilylcarbamide acid ester can be produced by reacting a carbamide acid ester whose nitrogen atom is linked to two hydrogen atoms, with a hexaorganodisilazane and a triorganohalogensilane, at a reaction temperature of about 50° C. and the N-triorganosilylcarbamide acid ester thus obtained can be separated from the ammonium halide by-product; however, this process requires large amounts of pyridine which is difficult to obtain. In addition, the desired product must be separated from the reaction medium by distillation. (See R. Nery, "Gaschromatographic Determination of Acetyl and Trimethylsilyl Derivatives of Alkyl Carbamates and their N-Hydroxy Derivatives" in "Analyst", Volume 94, 1969, pp 130 to 135).

Therefore, it is an object of this invention to provide a process for preparing N-triorganosilylcarbamide acid esters. Another object of this invention is to provide a process for preparing N-triorganosilylcarbamide acid esters in the absence of a solvent. A further object of this invention is to provide a process for preparing N-triorganosilylcarbamide acid esters substantially free of impurities.

The foregoing objects and others which will become apparent from the following description are accomplished in accordance with this invention, generally speaking, by providing a process for preparing N-triorganosilylcarbamide acid esters which comprises reacting in the substantial absence of solvent a carbamide acid ester whose nitrogen atom is linked to two hydrogen atoms, with a hexaorganodisilazane and a triorganohalosilane at a temperature of from 20° to 65° C. and thereafter separating the N-triorganosilylcarbamide acid ester from the ammonium halide by-product. It is preferred that the only contents of the reaction vessel are the reactants, the compounds resulting from the reaction and possibly compounds which are present in the gaseous phase at room temperature.

The resultant N-triorganosilylcarbamide acid ester can be separated from the ammonium halide by-product in the absence of substantial amounts of solvent within a short period of time and at temperatures of from 20° to 65° C. with an N-triorganosilylcarbamide acid ester yield of at least 95 percent by weight (theoretical) and a purity of from 97 to 99 percent by weight. These esters can be used for additional reactions without further purification. This is especially surprising since the carbamide acid esters are insoluble in both the hexaorganodisilazane and the triorganohalosilane at the indicated temperature, consequently the reaction is conducted in a heterogeneous system. Moreover, it was expected that the ammonium halide by-product, which formed in considerable quantity during the reaction, would retain large amounts of the desired esters, thereby necessitating a solvent wash in order to recover these esters.

The carbamide acid esters employed within the scope of this invention can be represented by the general formula

$H_2NCOOR$, in which R represents a monovalent hydrocarbon radical, preferably having from 1 to 18 carbon atoms or substituted monovalent hydrocarbon radicals in which the substituted radicals are inert under the reaction conditions.

Examples of suitable hydrocarbon radicals represented by R are alkyl radicals such as methyl, ethyl, n-propyl, isopropyl, n-butyl, sec.-butyl, tert.-butyl, n-amyl, isoamyl, n-hexyl, n-octyl, 2-ethylhexyl, n-dodecyl and n-octadecyl radicals; cycloalkyl radicals such as the cyclohexyl radical; alkenyl radicals such as the vinyl, allyl, ethylallyl and butadienyl radicals; cycloalkenyl radicals such as the cyclohexenyl radicals and aralkyl radicals such as the benzyl and beta-phenylethyl radicals. Examples of substituted hydrocarbon radicals represented by R are halogenated radicals such as the 3,3,3-trifluoropropyl radical, chlorophenyl and bromotolyl radicals; and cyanoalkyl radicals such as the betacyanoethyl radicals. Examples of preferred carbamide acid esters are methyl, ethyl and n-butylcarbamates.

Hexaorganodisilazanes which are employed in accordance with this invention are those represented by the general formula

$(R_3Si)_2NH$ in which the radicals represented by R may be the same or different are the same as above except that R can not be a tert.-butyl radical. Preferred examples of hexaorganodisilazanes are hexamethyldisilazane and divinyltetramethyldisilazane.

The triorganohalosilane employed in accordance with this invention can be represented by the general formula R₃SiX in which X represent a halogen atom, preferably chlorine or bromine and more preferably chlorine. The radical represented by R which may be the same or different is the same as above. Except for the tert.-butyl radical, the examples for the R radicals in the carbamide acid esters are equally applicable to the R radicals in the triorganosilanes. Preferred examples of triorganohalosilanes are trimethylchlorosilane and vinyldimethylchlorosilane.

It is preferred that the R radicals in the triorganohalosilanes employed in this invention be the same as the R radicals in the hexaorganodisilazane. The R radicals in the carbamide acid ester employed may be the same as or different from the R radicals in the hexaorganodisilazane and triorganosilane.

The exact nature of the chemical reaction is not known with certainty and the present invention is not intended to be limited to any particular mode of reaction. It may, however, be postulated that the reaction proceeds in accordance with the following equation.

3 H₂NCOOR + (R₃Si)₂NH + R₃SiX → 3 R₃SiNHCOOR + NH₄X

Thus, it is preferred that from 3.0 to 3.1 mols of carbamide acid ester be employed for each 1.0 to 1.05 mols of hexaorganodisilazane and each 1.0 mol of triorganohalosilane.

The sequence of addition of the reaction components is not critical and they may be introduced into the reaction vessel in any sequence.

The expression "that the reactants and the compounds produced as a result of the reaction as well as any compounds which are present in the gaseous phase at room temperature constitute the only contents of the reaction vessel" is intended to mean that while the presence of more or less unavoidable impurities of the reaction components or of inert solids as well as the use of solvents in amounts of up to 10 percent by weight based on the total weight of the reaction components is not preferred, it is, however, not to be excluded. The amount of solvent should not be in excess of 10 percent by weight and more preferably from 0 to 10 percent by weight based on the total weight of the reactants. When the solvent is below 10 percent, it need not be recovered or separated from the reaction product, thereby providing for a substantially greater yield as to space and time. It is preferable that the process of this invention be carried out at atmospheric pressure since this will result in lower production costs. Pressures above or below atmospheric pressure may of course be employed, if desired. It is desirable that the contents of the reaction vessel be agitated by means of shaking or stirring.

Termination of the reaction can be determined by ascertaining with the aid of wet litmus paper if hydrolyzable halogen, namely Si-linked halogen is still present. The reaction is preferably terminated as soon as the hydrolyzable halogen is no longer present. Generally, the reaction requires from 3 to 8 hours at 60° C.

The N-triorganosilylcarbamide acid ester resulting from the reaction of carbamide acid ester with hexaorganodisilazane and triorganohalosilane may be separated from ammonium halide by-product by any conventional technique known in the art such as by filtration.

The N-triorganosilylcarbamide acid esters obtained in accordance with this invention can be used, for example, to incorporate silyl groups onto compounds having at least one hydrogen atom which is linked to nitrogen, oxygen or sulfur, such as compounds which contain at least one of the following groups: —CH₂OH, ≡SiOH, —COOH, —NH₂, RNH, —NH—, —CONH₂, —SH, —COSH or ≡CSSH.

Various embodiments of this invention are further illustrated in the following examples in which all parts are by weight unless otherwise specified.

EXAMPLE 1

A mixture containing 3.06 mols of carbamide acid methyl ester, 1.03 mols of hexamethyldisilazane and 1.0 mol trimethylchlorosilane is heated for 3 hours at 60° C. under constant agitation. The product is separated from the ammonium chloride by filtration. The yield of N-trimethylsilylcarbamide acid methyl ester is 95 percent by weight of theoretical. The purity of the product is 98.5 percent by weight.

EXAMPLE 2

A mixture containing 3.06 mols of carbamide acid methyl ester, 1.03 mols of divinyltetramethyldisilazane and 1.0 mol vinyldimethylchlorosilane is heated for 7 hours at 60° C. under constant agitation. The product is separated from the ammonium chloride by filtration. The yield of N-vinyldimethylsilylcarbamide acid methyl ester is 95 percent by weight of theoretical. The product's purity is about 98 percent by weight.

EXAMPLE 3

A mixture containing 3.1 mols of carbamide acid ethyl ester, 1.05 mols of hexamethyldisilazane and 1.0 mol trimethylchlorosilane is heated for 3 hours at 60° C. under constant agitation. The product is separated from the ammonium chloride by vacuum filtration. The yield of N-trimethylsilylcarbamide acid ethyl ester is at least 95 percent of theoretical. The product's purity is 99 percent by weight.

EXAMPLE 4

A mixture containing 3.1 mols of carbamide acid ethyl ester, 1.05 mols of divinyltetramethyldisilazane and 1.0 mol of vinyldimethylchlorosilane is heated to 60° C. for 7 hours. The desired product is separated from the ammonium chloride by vacuum filtration. The yield of N-vinyldimethylsilylcarbamide acid ethyl ester is at least 95 percent by weight of theoretical. The product's purity is 98 percent by weight.

EXAMPLE 5

A mixture containing 3.1 mols of carbamide acid n-butyl ester, 1.05 mols hexamethyldisilazane and 1.0 mol trimethylchlorosilane is heated to 60° C. for 3 hours. The product is separated from the ammonium chloride by means of vacuum filtration. The yield of N-trimethylsilylcarbamide acid n-butyl ester is at least 95 percent by weight of theoretical. The product's purity is 98 percent by weight.

EXAMPLE 6

A mixture containing 3.1 mols of carbamide acid n-butyl ester, 1.05 mols of divinyltetramethyldisilazane and 1.0 mol vinyldimethylchlorosilane is heated to 60° C. for 8 hours. The product is then separated from the ammonium chloride by means of vacuum filtration. The yield of N-vinyldimethylsilylcarbamide acid n-butyl ester is at least 95 percent by weight of theoretical. The product's purity is 97.5 percent by weight.

Although specific examples of the invention have been described, it is not intended to limit the invention solely thereto, but to include all the variations and modifications falling within the spirit and scope of the appended claims.

What is claimed is:

1. A process for preparing N-triorganosilylcarbamide acid esters which comprises reacting in the substantial absence of a solvent a carbamide acid ester having two hydrogen atoms linked to its nitrogen atom with a hexaorganodisilazane and a triorganohalosilane at a temperature of from 20° to 65° C. and thereafter separating the thus formed N-triorganosilylcarbamide acid ester from ammonium halide by-product.

2. The process of claim 1 wherein the carbamide acid ester is represented by the general formula $$H_2NCOOR$$

in which R is selected from the group consisting of hydrocarbon radicals having from 1 to 18 carbon atoms and substituted monovalent hydrocarbon radicals in which the substituted radicals are inert under the reaction conditions.

3. The process of claim 2 wherein the carbamide acid ester is a carbamide acid n-butyl ester.

4. The process of claim 1 wherein the hexaorganodisilazane is represented by the general formula $$(R_3Si)_2NH$$

in which R is selected from the group consisting of monovalent hydrocarbon radicals having from 1 to 18 carbon atoms except a tert. butyl radical and substituted monovalent hydrocarbon radicals in which the substituted radicals are inert under the reaction conditions.

5. The process of claim 4 wherein the hexaorganodisilazane is hexamethyldisilazane.

6. The process of claim 4 wherein the hexaorganodisilazane is divinyltetramethyldisilazane.

7. The process of claim 1 wherein the triorganohalosilane is represented by the general formula $$R_3SiX$$

in which R is selected from the group consisting of monovalent hydrocarbon radicals having from 1 to 18 carbon atoms, except a tert.-butyl radical and substituted monovalent hydrocarbon radicals in which the substituted radicals are inert under the reaction conditions and X is a halogen atom.

8. The process of claim 7 wherein the triorganohalosilane is trimethylchlorosilane.

9. The process of claim 7 wherein the triorganohalosilane is vinyldimethylchlorosilane.

10. The process of claim 1 wherein the amount of solvent present is below 10 percent by weight based on the weight of the reactants.

11. The process of claim 1 wherein the hexaorganodisilazane is hexamethyldisilazane and the triorganohalosilane is trimethylchlorosilane.

12. The process of claim 11 wherein the hexaorganodisilazane is divinyltetramethyldisilazane.

* * * * *